(12) United States Patent
Izumori et al.

(10) Patent No.: US 6,294,369 B1
(45) Date of Patent: Sep. 25, 2001

(54) L-RIBOSE ISOMERASE, ITS PREPARATION AND USES

(75) Inventors: Ken Izumori, Kagawa; Keiji Tsusaki, Okayama, both of (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 0 days.

(21) Appl. No.: 09/524,014

(22) Filed: May 31, 2000

Related U.S. Application Data

(62) Division of application No. 09/122,642, filed on Jul. 27, 1998, now Pat. No. 6,037,153, which is a division of application No. 08/856,006, filed on May 14, 1997, now Pat. No. 5,846,804.

(30) Foreign Application Priority Data

May 16, 1996 (JP) .................................................. 8-144831
Oct. 1, 1996 (JP) .................................................. 8-280113
Mar. 19, 1997 (JP) .................................................. 9-91316

(51) Int. Cl.$^7$ .............................. C12N 9/90; C12N 1/20
(52) U.S. Cl. ..................... 435/233; 435/252.1; 435/94; 435/105; 536/1.11; 536/125
(58) Field of Search .................................. 435/233, 105, 435/252.1, 94; 536/1.11, 125

(56) References Cited

PUBLICATIONS

Shimonishi et al, J. Ferment. Bioengineer., 81(6):493–497 (1996).*
Holt et al, Bergey's Manual of Determinative Bacteriology, 9th Ed., pp. 73, 103, 129 (1994).*
"List of Cultures" Institute for Fermentation, Osaka (IFO), 9th Ed., pp. V–VI, 95, 136 (1992).*
Izumori et al, "Purification, Crystallization, and Properties of D–ribose Isomerase from Mycobacterium Smegmatis", J. Biol. Chem. 250(20):8085–8087 (1975).*
Izumori et al, "Induction of D–ribose Isomerase by L–ribose in Mycobacterium Smegmatis", Agric. Biol. Chem. 44(1):223–225 (1980).*
Trimur et al, "Isolation and Characterization of *Escherichia coli* Mutants Able to Utilize the Novel Pentose L–ribose", J. Bacteriol. 137(8):2459–2464 (1991).*

* cited by examiner

*Primary Examiner*—Francisco Prats
(74) *Attorney, Agent, or Firm*—Browdy and Neimark

(57) ABSTRACT

An L-ribose isomerase which isomerizes aldoses such as L-ribose, D-lyxose, D-talose, D-mannose, L-allose and L-gulose into their corresponding ketoses such as L-ribulose, D-xylulose, D-tagatose, D-fructose, L-psicose and L-sorbose. The enzymatic reaction is a reversible equilibrium reaction. The L-ribose isomerase can be obtained from microorganisms of the genus Acinetobacter.

7 Claims, 3 Drawing Sheets

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
       (A) LENGTH: 5 amino acids
       (B) TYPE: amino acid
       (C) STRANDEDNESS: single
       (D) TOPOLOGY: linear (ii) MOLECULE TYPE: peptide (v) FRAGMENT TYPE: N-terminal fragment (xi) SEQUENCE DESCRIPTION: SEQ ID NO: 1:

Thr Arg Thr Ser Ile
1               5

(2) INFORMATION FOR SEQ ID NO: 2:

(i) SEQUENCE CHARACTERISTICS:
       (A) LENGTH: 26 amino acids
       (B) TYPE: amino acid
       (C) STRANDEDNESS: single
       (D) TOPOLOGY: linear (ii) MOLECULE TYPE: peptide (v) FRAGMENT TYPE: N-terminal fragment (xi) SEQUENCE DESCRIPTION: SEQ ID NO: 2:

Thr Arg Thr Ser Ile Thr Arg Arg Glu Tyr Asp Glu Trp Val Arg Glu
1               5                   10                  15

Ala Ala Ala Leu Gly Lys Ala Leu Arg Tyr
            20                  25

L-RIBOSE ISOMERASE, ITS PREPARATION AND USES

This is a division of parent application Ser. No. 09/122,642, filed Jul. 27, 1998, now U.S. Pat. No. 6,037,153, which in itself is a division of Ser. No. 08/856,006 filed May 14, 1997 now U.S. Pat. No. 5,846,804.

BACKGROUND OF THE INVENTION

1. Field of the Invention

The present invention relates to an L-ribose isomerase, its preparation and uses, more particularly, relates to an L-ribose isomerase which converts L-ribose into L-ribulose and vice versa, preparation thereof, microorganisms capable of producing the L-ribose isomerase, and a process for producing ketoses and aldoses using the L-ribose isomerase.

2. Description of the Prior Art

Biochemical industries have been developing in these days, and rare saccharides which had been put aside are in great demand in the field of saccharide chemistry. Thus, the establishment of these rare saccharides is strongly required. Although such rare saccharides can be produced by organic chemical methods, the production conditions are generally crucial and the yields of desired products are relatively low. Therefore, the organic chemical methods are not satisfactory as an industrial scale production. While enzymatic saccharide-conversion methods may be imagined as biochemical methods for producing rare saccharides but there was reported no isomerase, which acts on L-ribose or D-talose as a rare saccharide, and was not established the production method for such rare saccharides.

SUMMARY OF THE INVENTION

It has been strongly required an industrial-scale production method for rare saccharides such as L-ribose and D-talose.

To attain the object the present inventors studied on an L-ribose isomerase and extensively screened microorganisms which produce such an enzyme. As a result, the inventors found that a newly isolated microorganism of the species *Acinetobacter calcoaceticus* LR7C strain, isolated from a soil in Miki-machi, Kita-gun, Kagawa, Japan, produces an L-ribose isomerase. The inventors also found that the L-ribose isomerase facilitates the production of rare saccharides when acts on aldoses or ketoses as substrates and established the present invention.

BRIEF DESCRIPTION OF THE ACCOMPANYING DRAWINGS

DETAILED DESCRIPTION OF THE INVENTION

Figure 1:
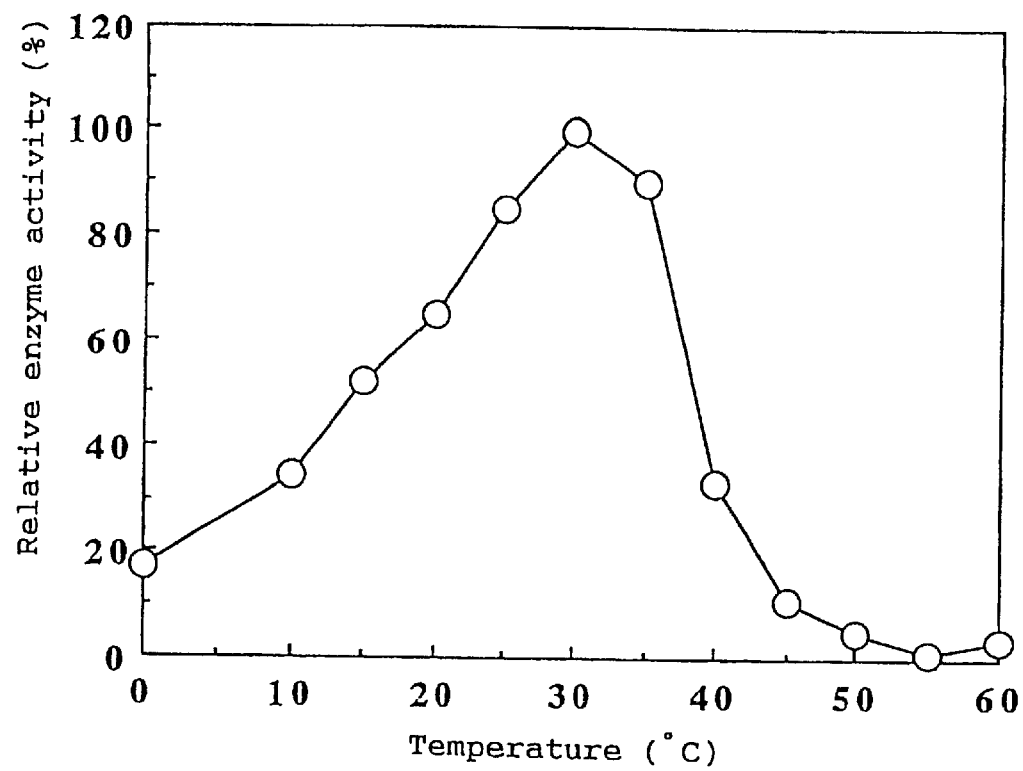
FIG. 1 shows the influence of temperature on the enzymatic activity of an L-ribose isomerase derived from *Acinetobacter calcoaceticus*.

The present invention relates to an L-ribose isomerase, its preparation and uses, more particularly, relates to an L-ribose isomerase which converts L-ribose into L-ribulose and vice versa, preparation thereof, microorganisms capable of producing the L-ribose isomerase, and a process for producing ketoses and aldoses using the L-ribose isomerase.

Followings are the identification results of the microorganism of the genus Acinetobacter, i.e., *Acinetobacter calcoaceticus* LR7C strain (FERM BP-5335).

Identification Results of *Acinetobacter calcoaceticus* LR7C Strain:

A. Morphology

Characteristics of cells when incubated at 27° C. in nutrient broth agar Usually existing in a single rod form of $1.0–1.5 \times 1.5–2.5$ μm;

Motility: Positive (rotatory or vibratory motility);

Asporogenicity: Positive;

Flagellum: Positive;

Gram stain: Negative;

B. Cultural properties (1) Characteristics of colony formed when incubated at 27° C. in nutrient agar plate with broth Shape: Circular colony having a diameter of about 0.1–1 mm after 2 days' incubation;

Rim: Entire;

Projection: Hemispherical shape;

Gloss: Dull;

Surface: Smooth;

Color: Semitransparency, pale yellow;

(2) Characteristics of colony formed when incubated at 27° C. in slant nutrient agar with broth Growth: Satisfactory;

Shape: Thread-like;

(3) Characteristics of colony formed when incubated at 27° C. in slant nutrient agar with trypton soya broth Growth: Satisfactory;

Shape: Thread-like; and (4) Not liquefying gelatin when stab-cultured at 27° C. in nutrient gelatin with broth. C. Physiological properties (1) Reduction of nitrate: Positive;

(2) Accumulation of poly-β-hydroxy butyrate: Negative;

(3) Methyl red test: Negative;

(4) VP-Test: Negative;

(5) Formation of indole: Negative;

(6) Formation of hydrogen sulfide: Negative;

(7) Hydrolysis of starch: Negative;

(8) Utilization of citric acid: Positive;

(9) Formation of pigment: Negative;

(10) Oxidase: Negative;

(11) Catalase: Positive;

(12) Growth conditions: Growing at a temperature in the range of 20–37° C.;

(13) Oxygen requirements: Aerobic;

(14) Formation of acid from D-glucose: Positive;

(15) Hemolysis: Negative;

(16) β-Xylosidase: Negative;

(17) Utilization of carbon source Utilizing glutaric acid, malonic acid, phenyl lactic acid, azelaic acid, D-malic acid, ethanol, 2,3-butanediol, aconitic acid, D-ribose, D-xylose, L-arabinose and D-glucose;

(18) Utilization of nitrogen source Utilizing L-phenyl alanine, L-histidine, L-aspartic acid, L-leucine, L-tyrosine, β-alanine, L-arginine and L-ornithine but not utilizing histamine;

(19) DNase: Positive;

(20) Formation of 3-ketolactose: Negative; and

(21) Molt % guanine (G) plus cytosine (C) of DNA: 42%.

Based on these mycological properties, the microorganism was compared with those of known microorganisms with reference to *Bergey's Manual of Determinative Bacteriology*, Ninth Edition (1994). As a result, it was revealed that the microorganism was identified as a novel microorganism of the genus Acinetobacter. The present inventors identified this microorganism as the one of the species *Acinetobacter calcoaceticus* based on the data of not growing at 41° C., negative hemolysis and gelatin hydrolysis, positive acid formation from glucose, and conditions of utilizing carbon and nitrogen sources.

From these results, the present inventors named the microorganism "*Acinetobacter calcoaceticus* LR7C" and deposited it on Dec. 14, 1995, in National Institute of Bioscience and Human-Technology Agency of Industrial Science and Technology, Ibaraki, Japan. The deposition of the microorganism was accepted on the same day and has been maintained by the institute under the accession number of FERM BP-5335.

In addition to the above-identified microorganism, other strains of the genus Acinetobacter and mutants thereof can be suitably used in the present invention as long as they produce the L-ribose isomerase according to the present invention. The above mutants can be obtained by physically treating microorganisms of the genus Acinetobacter with ultraviolet ray or γ-ray, chemically treating the microorganisms with nitrosoguanidine, or by successively culturing the microorganisms in nutrient culture media containing D-lyxose to stably produce the present L-ribose isomerase and to increase the enzyme yield. Any other microorganism can be used in the present invention as long as it produces the present L-ribose isomerase. It is possible to produce the L-ribose isomerase by expressing the isomerase in transformants into which a gene encoding the isomerase is introduced. If necessary, protein engineering techniques can be used to increase the thermal stability of the present L-ribose isomerase or to widen the range of pH stability. Any nutrient culture medium such as synthetic- or natural-nutrient culture medium can be used in the invention as long as the above microorganisms can grow therein and produce the present L-ribose isomerase. One or more carbon-containing substances such as aldoses, ketoses and sugar alcohols can be used in the invention as carbon sources. Usually, D-lyxose can be advantageously used as carbon sources for the culture media. The nitrogen sources used in the present invention include inorganic nitrogen-containing compounds such as ammonium salts and nitrates and organic nitrogen-containing compounds such as urea, corn steep liquor, casein, peptone, yeast extract and beef extract. The inorganic ingredients used in the present invention include calcium salts, magnesium salts, potassium salts, sodium salts and phosphates. The microorganisms used in the invention can be cultured under aerobic conditions at a temperature of, usually, about 10–40° C., preferably, about 20–35° C., and at a pH of about 5–9, preferably, about 6–8.5.

After completion of the culture of microorganisms, the present L-ribose isomerase is recovered from the culture. The cells in themselves can be used as an enzymatic agent because the enzyme mainly exists intracellularly. The intracellular enzyme can be extracted from the cells by a conventional technique, and the extracted enzyme can be used intact as a crude enzyme or used after purified by a conventional method. For example, extracts of homogenized cells can be purified by two or more techniques such as fractionations using polyethylene glycol, ion-exchange chromatographies, and gel filtration chromatographies to obtain enzyme preparations with an electrophoretically single protein band.

The present L-ribose isomerase activity is assayed as follows: Mix 0.05 ml of 0.5 M glycine-sodium hydroxide buffer (pH 9.0), 0.05 ml of 0.05 M L-ribose, and an appropriate volume of an enzyme solution sufficient to give a total volume of 0.5 ml. Incubate the resulting solution at 30° C. for an enzymatic reaction and quantify the amount of formed L-ribose by the cysteine-carbazole method. One unit activity of the present L-ribose isomerase is defined as the amount of enzyme which forms one μmole of L-ribose per minute.

In addition to L-ribose, the present L-ribose isomerase acts on aldoses such as D-lyxose, D-talose, D-mannose, L-allose and L-gulose to isomerize them into their corresponding ketoses.

The present L-ribose isomerase should not necessarily be purified to the highest possible level. For example, microorganisms, containing the L-ribose isomerase and being treated with toluene, can be suitably used intact in industrial-scale saccharide-transferring reactions. Microorganisms with the present L-ribose isomerase activity and partially purified preparations of the isomerase can be immobilized by conventional immobilization methods such as entrapping, adsorption and covalent bonding methods. The immobilized enzyme can be repeatedly used batchwise or continuously used after packed in columns.

The reaction mixtures thus obtained usually contain both aldoses and ketoses. In general, the mixtures can be purified by two or more techniques of filtration using filter aids, filters and membrane filters, centrifugation to remove insoluble substances, decoloration with activated charcoals, and desalting using ion exchangers in H- and OH-form. The resulting mixtures can be concentrated to obtain syrupy products or dried into powdery solid products. If necessary, higher level crystallization steps can be employed: For example, fractionations using cation exchangers in alkaline metal and/or alkaline earth metal form or anion exchangers in bisulfite and/or boric acid form, and column chromatographies using silica gels readily produce high-purity saccharides. When the obtained saccharides are crystallizable, they can be arbitrarily prepared into crystalline products by conventional crystallization techniques. For example, the above reaction mixtures or saccharide solutions, either treated with or without appropriate purification methods, are admixed with one or more organic solvents in general such as lower alkyl alcohols including methanol, ethanol and isopropyl alcohol or concentrated and/or allowed to stand at relatively-low temperatures. These methods can be combined to obtain supersaturated solutions of the above saccharides, followed by crystallizing the solutions and separating the crystals to obtain solid products containing crystals. These saccharide products can be used as chemical reagents and used in food industries as sweeteners and quality-improving agents and in pharmaceutical and chemical industries as materials and intermediates.

Among these saccharides, D-ribose, an isomer of L-ribose, is an essential component for DNA correlating deeply with cell growth. Therefore, L-ribose or derivatives thereof can be used as a replication inhibitory agent for nucleic acids: Examples of such an inhibitory agent include pharmaceuticals such as antiseptics, antiviral agents, anti-AIDS agents and antitumor agents. As is described above, L-ribose is readily prepared from L-ribulose by using the present L-ribose isomerase. The L-ribulose is not restricted to its origin: For example, the saccharide can be readily prepared by oxidation reactions using microorganisms of the genera Gluconobacter and Acetobacter, i.e., the species *Gluconobacter frateurii* and *Acetobacter aceti*. The following experiments explain the present invention in detail:

EXPERIMENT 1

Preparation of L-ribose Isomerase from *Acinetobacter calcoaceticus* LR7C

A liquid nutrient culture medium, consisting of 0.5 w/v % yeast extract, 0.5 w/v % polypeptone, 0.5 w/v % salt and water, was adjusted to pH 7.0. Two liters of the medium was placed in a 2.5-L jar fermenter, sterilized by an autoclave at 120° C. for 20 min, cooled and inoculated with a seed culture of *Acinetobacter calcoaceticus* LR7C (FERM BP-5335), which had been cultured for 4 days in a nutrient culture medium containing D-lyxose as a carbon source, which were then cultured at 30° C. for 14 hours under aeration-agitation conditions. The culture medium was centrifuged to obtain cells in a yield of about 15 g wet cells per one L of the culture medium. The wet cells were in a conventional manner disrupted with aluminum powder, admixed with 0.05 M Tris-HCl. buffer (pH 7.5) to extract the desired enzyme, and centrifuged to obtain a 200-ml supernatant as a crude enzyme solution, having a total enzyme activity of 2,870 units and a specific activity of 1.73 units/mg protein.

EXPERIMENT 2

Purification of L-ribose Isomerase

EXPERIMENT 2-1

Polyethylene Glycol Fractionation

The crude enzyme solution in Experiment 1 was ice-chilled, admixed with 0.01 M manganese chloride, allowed to stand for 30 min, and centrifuged to remove insoluble substances. To the resulting supernatant was added polyethylene glycol powder to give a final concentration of 15 w/v % and dissolved therein under stirring conditions, followed by centrifuging the mixture to remove the formed insoluble substances. The resulting supernatant was mixed with polyethylene glycol to give a final concentration of 25 w/v % and dissolved therein under stirring conditions, and the formed insoluble substances were centrifugally collected.

EXPERIMENT 2-2

Ion-exchange Chromatography

The sediments in Experiment 2-1 were dissolved in 0.05 M Tris-HCl buffer (pH 7.5), and the residual insoluble substances were removed by centrifugation to obtain a 13-ml supernatant which was then fed to a column packed with "DEAE-TOYOPEARL® 650M", a slightly alkaline anion-exchanger commercialized by Tosoh Corporation, Tokyo, Japan, to adsorb the desired enzyme on the exchanger, followed by eluting the enzyme from the column with a liner gradient solution of potassium chloride which increases from 0 M to 0.5 M and collecting fractions with an L-ribose isomerase activity.

EXPERIMENT 2-3

Gel Filtration Chromatography

The fractions with an L-ribose isomerase activity in Experiment 2-2 were concentrated, and the concentrate was fed to a column packed with "SEPHADEX® G-150", a bead-like dextran gel commercialized by Pharmacia LKB Biotechnology AB, Uppsala, Sweden, and eluted with 0.05 M Tris-HCl buffer (pH 7.5) to obtain fractions with an L-ribose isomerase activity. Table 1 shows the protein amount, enzyme activity, enzyme yield, and enzyme purification degree in each purification step.

TABLE 1

| Purification step | Protein (mg) | Enzyme activity (unit) | Yield (%) | Purification degree |
|---|---|---|---|---|
| Crude enzyme | 1,660 | 2,870 | 100 | 1.0 |
| PEG fraction | 450 | 2,570 | 90 | 3.3 |
| DEAE-TOYOPEARL ® | 79.8 | 1,180 | 41 | 8.6 |
| SEPHADEX ® | 32.9 | 796 | 28 | 14 |

Purity inspection by polyacrylamide gel disk electrophoresis for the finally purified enzyme, obtained as an eluate in the gel filtration using "SEPHADEX® G-150" in Table 1, revealed that the enzyme was purified up to show a single protein band, meaning that the enzyme was an electrophoretically highly-purified enzyme.

EXPERIMENT 3

Property of L-ribose Isomerase

Using a purified L-ribose isomerase, obtained by the method in Experiment 2, the physicochemical properties were studied.

EXPERIMENT 3-1

Action

When acting on L-ribose or L-ribulose in accordance with the method for assaying the present L-ribose isomerase activity, the purified L-ribose isomerase formed L-ribulose from L-ribose and vice versa. The enzymatic reaction is a reversible equilibrium reaction.

EXPERIMENT 3-2

Substrate specificity

In accordance with the method for assaying the present L-ribose isomerase activity, the purified L-ribose isomerase activity for aldoses as substrates was assayed. Table 2 shows relative activities of the enzyme for the aldoses when the relative activity of the enzyme for L-ribose was regarded as 100.

TABLE 2

| Substrate | Relative activity (%) |
|---|---|
| L-Ribose | 100 |
| D-Lyxose | 50 |
| D-Talose | 44 |
| D-Mannose | 3 |
| L-Allose | 2 |
| L-Gulose | 2 |

As is evident from the results in Table 2, the L-ribose isomerase showed the highest activity on L-ribose. The L-ribose isomerase acted on other aldoses such as L-lyxose, D-talose, D-mannose, L-allose and L-gulose. These enzymatic reactions were reversible reactions, and the enzyme also acted on L-ribulose, D-xylulose, D-tagatose, D-fructose, L-psicose and L-sorbose as substrates corresponding to the above aldoses, respectively. Table 3 shows the data of ketoses and aldoses, produced from the above substrates, which were confirmed by ion-exchange chromatography, high-performance liquid chromatography, thin-layer chromatography, etc.

TABLE 3

| Material | Product |
| --- | --- |
| L-Ribose | L-Ribulose |
| D-Lyxose | D-Xylulose |
| D-Talose | D-Tagatose |
| D-Mannose | D-Fructose |
| L-Allose | L-Psicose |
| L-Gulose | L-Sorbose |
| L-Ribulose | L-Ribose |
| D-Xylulose | D-Lyxose |
| D-Tagatose | D-Talose |
| D-Fructose | D-Mannose |
| L-Psicose | L-Allose |
| L-Sorbose | L-Gulose |

As is evident from the results in Table 3, the present L-ribose isomerase acts on aldoses to convert them into their corresponding ketoses and vice versa. These enzymatic conversion reactions share a common enzymatic reaction mode. Chemical formula 1 is an example of the reaction mode. Chemical formula 1;

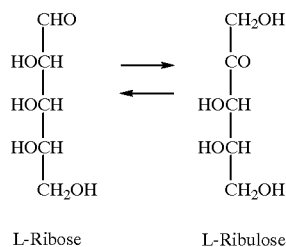

Figure 4:
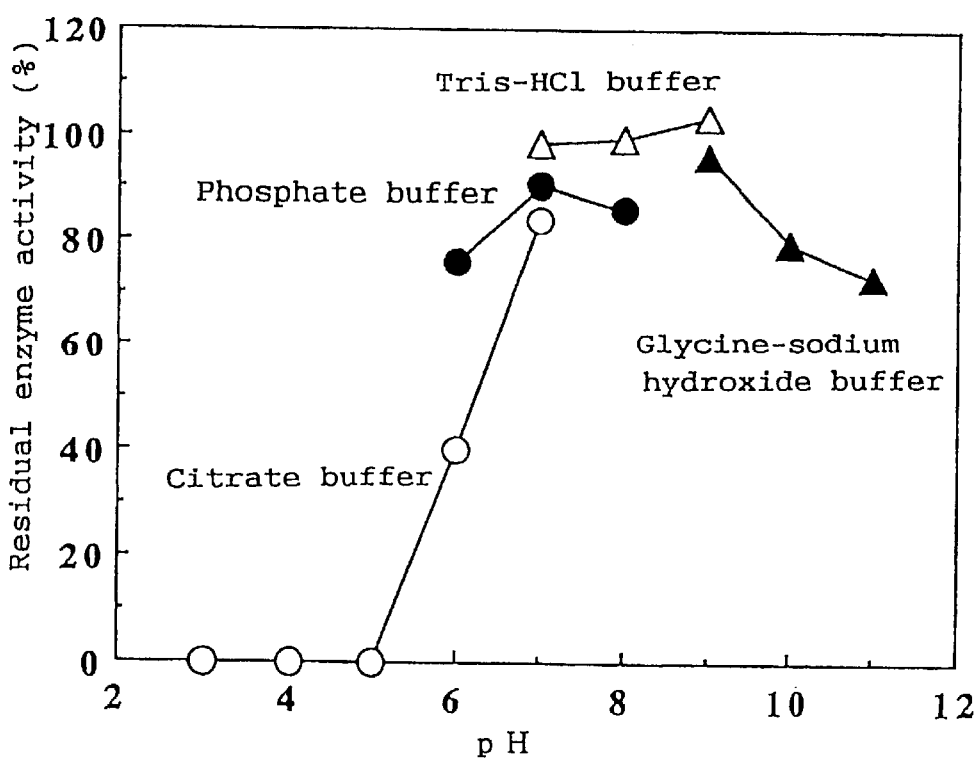
FIG. 4 shows the pH stability of an L-ribose isomerase derived from *Acinetobacter calcoaceticus*.
Figure 5:
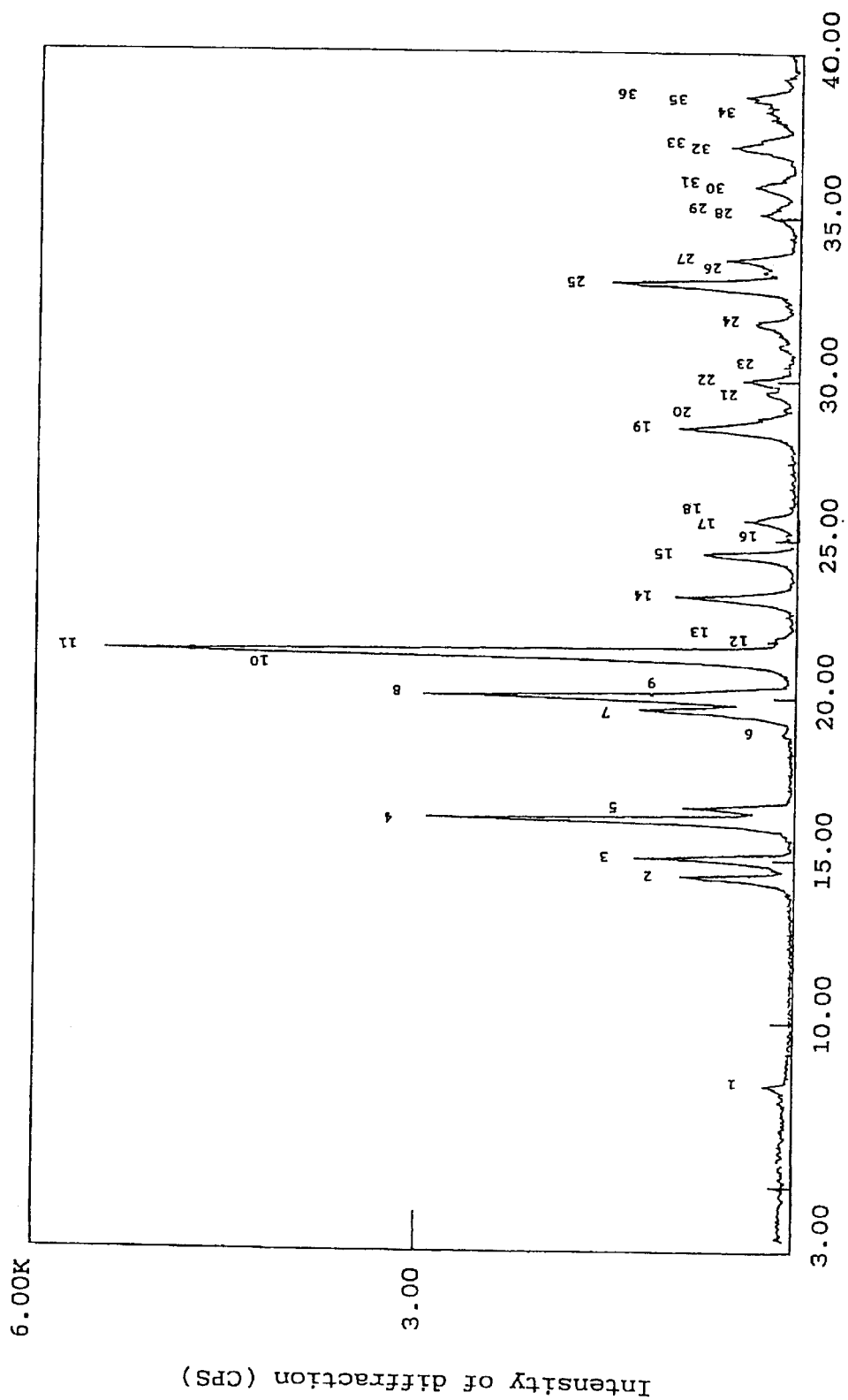
FIG. 5 is an X-ray diffraction figure for an L-ribose crystal with the highest purity obtained by the present invention, determined on powdery x-ray diffraction analysis using CuKa ray. The numerals in the figure are the peak numbers for peaks each.

The enzymatic reaction of the present L-ribose isomerase is a reversible reaction. FIG. 4 shows the results of the quantitative relationship of reversible equilibrium reactions between aldoses and ketoses under the conditions used for assaying the present L-ribose isomerase activity.

TABLE 4

| |
| --- |
| L-Ribose:L-Ribulose = 70:30 |
| D-Lyxose:D-Xylulose = 70:30 |
| D-Talose:D-Tagatose = 12:88 |
| D-Mannose:D-Fructose = 30:70 |
| L-Allose:L-Psicose = 40:60 |
| L-Gulose:L-Sorbose = 25:75 |

The Km, Michaelis constant, of the present L-ribose isomerase to L-ribose was 44 mM.

EXPERIMENT 3-3

Molecular Weight (1) About 25,000–35,000 daltons on polyacrylamide gel electrophoresis (SDS-PAGE);
(2) About 110,000–130,000 daltons on gel filtration method;
   The molecular weight on gel filtration, about 4 times higher than that on SDS-PAGE, indicates that the present L-ribose isomerase exists in tetramer.

EXPERIMENT 3-4

Isoelectric Point (pI)

The present L-ribose isomerase has a pI of about 4.0–5.5 on isoelectrophoresis using an agarose plate.

EXPERIMENT 3-5

Inhibition of Activity

The activity of the present L-ribose isomerase is slightly inhibited by L-arabitol and ribitol.

EXPERIMENT 3-6

Optimum Temperature

The optimum temperature of the present L-ribose isomerase was studied in accordance with the method for assaying the present L-ribose isomerase activity. As is shown in FIG. 1, the optimum temperature was about 30° C. when incubated at pH 9.0 for 10 min.

EXPERIMENT 3-7

Optimum pH

Figure 2:
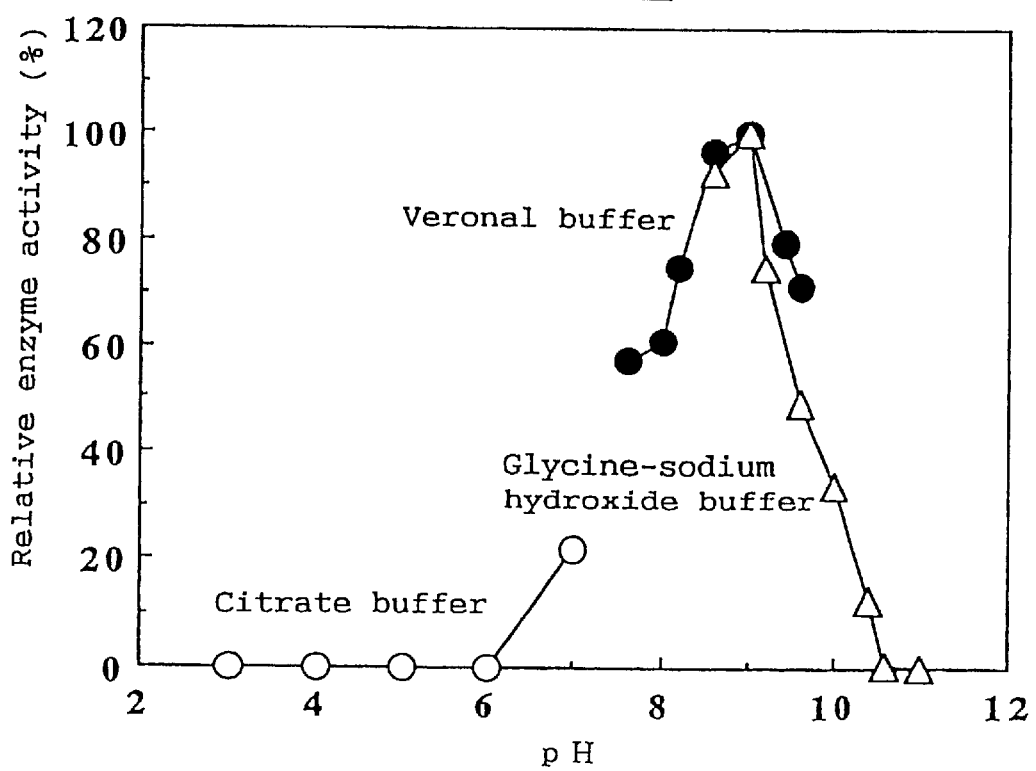
FIG. 2 shows the influence of pH on the enzymatic activity of an L-ribose isomerase derived from *Acinetobacter calcoaceticus*.

The optimum pH of the present L-ribose isomerase was studied in accordance with the method for assaying the present L-ribose isomerase activity. As is shown in FIG. 2, the optimum pH was about 8–9 when incubated at 30° C. for 10 min. FIG. 2 shows the results of assay using citrate buffer, Veronal buffer, and glycine-sodium hydroxide buffer which are respectively indicated by the symbols "○", "●" and "Δ".

EXPERIMENT 3-8

Thermal Stability

Figure 3:
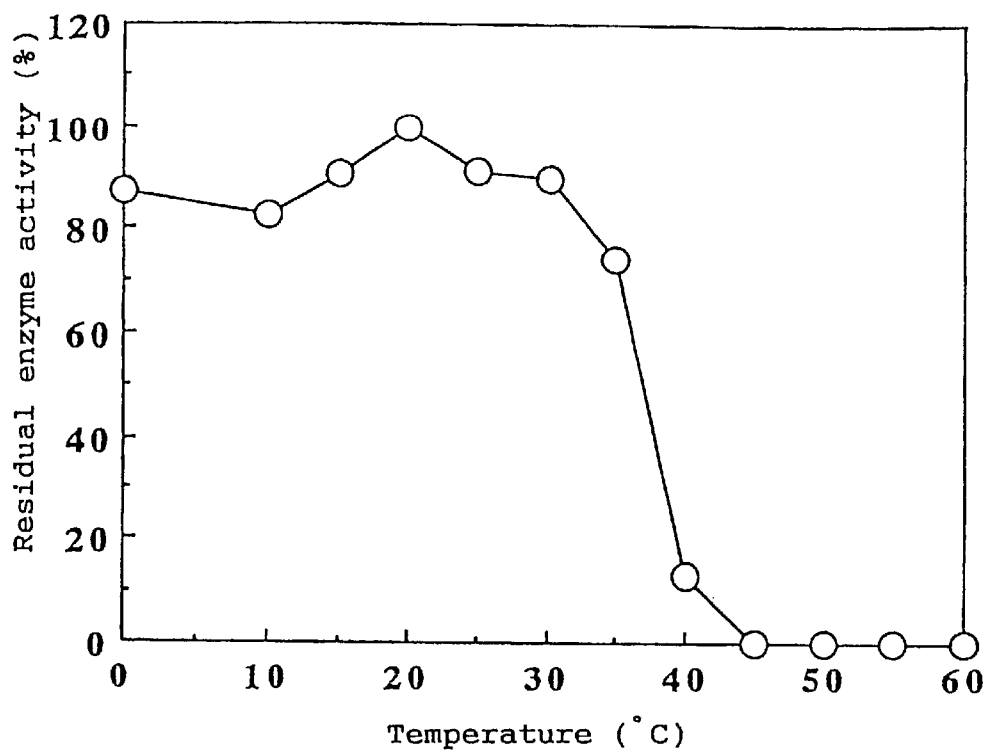
FIG. 3 shows the thermal stability of an L-ribose isomerase derived from *Acinetobacter calcoaceticus*.

The thermal stability of the present L-ribose isomerase was studied in accordance with the method for assaying the present L-ribose isomerase activity. As is shown in FIG. 3, the L-ribose isomerase was stable up to a temperature of about 30° C. when incubated at pH 9.0 for 10 min.

EXPERIMENT 3-9 pH Stability

The pH stability of the present L-ribose isomerase was studied in accordance with the method for assaying the L-ribose isomerase. As is shown in FIG. 4, the isomerase was stable at a pH of about 7–9 when incubated at 4° C. for 24 hours. FIG. 4 shows the results of assay using citrate buffer, phosphate buffer, Tris-HCl buffer, and glycine-sodium hydroxide buffer which are respectively indicated by the symbols "○", "●", "Δ" and "▲".

Based on these data, the optimum pH and pH stability of the present L-ribose isomerase are substantially equal, meaning that the isomerase has an advantageous feature when used in an industrial-scale production.

EXPERIMENT 3-10

N-Terminal Amino Acid Sequence

A purified enzyme preparation, obtained by the method in Experiment 2–3, was dialyzed against distilled water, and an about 80 μg of the enzyme with respect to a protein content was used as a sample for analyzing the N-terminal amino acid sequence. "PROTEIN SEQUENCER MODEL 473A", a protein sequencer commercialized by Applied Biosystems Inc., Foster City, USA, determined the amino acid sequence up to the fifth amino acid residue from the N-terminal to be the one in SEQ ID NO: 1. More detail analysis of the above sample revealed that the enzyme contains the amino acid sequence of SEQ ID NO: 2 as an N-terminal partial amino acid sequence.

The followings are the preferred Examples according to the present invention:

EXAMPLE 1

Production of Ketoses for Aldoses

Using a purified L-ribose isomerase obtained by the method in Experiment 2, ketoses were produced from aldoses. L-Ribose, D-lyxose, D-talose, D-mannose, L-allose and L-gulose were used as aldoses. While keeping 10 ml of 0.05 M aldose solution at pH 9, 50 units of the purified L-ribose isomerase was added to the aldose solution, followed by the incubation at 30° C. for 10 hours. The reaction mixture was treated with activated charcoal and subjected to deionization and fractionation by column chromatography using a cation exchanger in $Ca^{++}$-form. The resulting fractions containing a desired product was concentrated in vacuo to obtain a purified product. Analyses on high-performance liquid chromatography and thin-layer chromatography revealed that the relationship between aldoses as materials and ketoses as products was substantially the same as that of Table 3.

EXAMPLE 2

Production of Aldoses from Ketoses

Using a purified L-ribose isomerase obtained by the method in Experiment 2, aldoses were produced from ketoses. L-Ribulose, D-xylulose, D-tagatose, D-fructose, L-psicose and L-sorbose were used as ketoses. While keeping 10 ml of 0.05 M ketose solution at pH 9, 50 units of the purified L-ribose isomerase was added to the ketose solution, followed by the incubation at 30° C. for 10 hours. The reaction mixture was treated with activated charcoal and subjected to deionization and fractionation by column chromatography using a cation exchanger in Na+-form. The resulting fractions containing a desired product was concentrated in vacuo to obtain a purified product. Analyses on high-performance liquid chromatography and thin-layer chromatography revealed that the relationship between aldoses as materials and ketoses as products was substantially the same as that of Table 3.

EXAMPLE 3

Production of L-ribose

In accordance with the method in Example 2, 10 units of a purified L-ribose isomerase was added to 25 ml of 0.1 M L-ribulose, followed by the incubation at 30° C. for 15 hours to convert L-ribulose into L-ribose The reaction mixture was in a conventional manner decolored with activated charcoal, desalted and purified with ion exchangers in H- and $CO_3$-form, and fractionated by column chromatography using an anion exchanger in bisulfite-form heated to 40° C. to obtain a purified L-ribose. The yield of the purified L-ribose to the material L-ribulose was about 60%, on a dry solid basis (d.s.b.). The product can be arbitrarily used in food products, cosmetics, pharmaceuticals, and their materials as a sweetener, quality-improving agent, humectant, and replication inhibitory agent for nucleic acids.

EXAMPLE 4

Production of D-talose

In accordance with the method in Example 2, 10 units of a purified L-ribose isomerase was added to 50 ml of 0.1 M D-tagatose, followed by the incubation at 30° C. for 20 hours to convert D-tagatose into D-talose. The reaction mixture was in a conventional manner decolored with activated charcoal, desalted and purified with ion exchangers in H- and $CO_3$-form, and fractionated by column chromatography using a cation exchanger in $Ca^{++}$-form, followed by concentrating the fractions containing a desired product to obtain a D-talose crystal. The yield of the obtained D-talose to the material D-tagatose was about 10%, d.s.b. The product can be arbitrarily used in food products, cosmetics, pharmaceuticals, and their materials as a sweetener, quality-improving agent and humectant.

EXAMPLE 5

Production of L-ribose from Ribitol

One hundred ml aliquots of a nutrient culture medium, consisting of 2 w/v % trypton soya broth, one w/v % glycerol and deionized water, were distributed to ten 500-ml shaking flasks, followed by autoclaving the flasks at 120° C. for 20 min. Thereafter, the flasks were cooled and inoculated with a seed culture of *Gluconobacter frateurii* (IFO 3254) using a platinum loop, followed by incubation at 30° C. for 2 days under shaking conditions. After completion of the culture, the cells were collected by centrifugation, and about 10 g wet alive cells was mixed with 100 ml of 0.05 M Tris-HCl buffer (pH 7.0) containing 5 w/v % ribitol. The mixture solution in a volume of 100 ml was placed in a 500-ml shaking flask, and incubated at 30° C. for 20 hours under shaking conditions to convert ribitol into L-ribulose. Thereafter, the culture was centrifuged to remove cells, and the resulting supernatant was in a conventional manner decolored with activated charcoal, desalted with "DIAION SK1B (H-form)" and "DIAION WA30 (OH-form)", both of which are cation exchangers of Mitsubishi Chemical Corporation, Tokyo, Japan, and concentrated in vacuo to obtain a transparent syrup with a concentration of about 60 w/w %. The syrup was fractionated by column chromatography using "DOWEX 50W-X4", a cation exchanger in $Ca^{++}$-form commercialized by The Dow Chemical Co., Midland, Mich., USA, to obtain high L-ribulose content fractions which were then concentrated into an about 70 w/w % syrup. High-performance liquid chromatographic (HPLC) analysis using a column, 8×300 mm, packed with "MCIGEL CK-08EC", a gel in $Ca^{++}$-form commercialized by Mitsubishi Chemical Corporation, Tokyo, Japan, revealed that the product contained at least 97 w/w % L-ribulose, d.s.b. The yield of L-ribulose to the material ribitol was about 90%, d.s.b.

Using the obtained L-ribulose, L-ribose was prepared as follows: According to the method in Experiment 1, about 50 g wet cells was obtained by centrifuging a culture of microorganisms and treated with toluene. The resulting cells were kneaded with 100 ml of 2.5 w/v % sodium alginate. The slurry containing cells was dropped into 0.1 M $CaCl_2$ solution, which was being stirred by a magnetic stirrer, to form gels with a diameter of about 2 mm. The gels were filtered to obtain an immobilized enzyme with an L-ribose isomerase activity of about 5,000 units. An L-ribulose syrup obtained by the above method was diluted with water into an about 1.0 M solution which was then mixed with about 50 units/g L-ribulose of the immobilized enzyme, and allowed to react at pH 8.5 and 10° C. for 15 hours to convert L-ribulose into L-ribose. The immobilized enzyme was collected by filtration, and the filtrate was similarly as in Example 3 decolored, desalted, and fractionated by column chromatography to obtain high L-ribose content fractions while removing high L-ribulose content fractions. The high L-ribose content fractions were pooled, concentrated, crystallized by the addition of a seed crystal under stirring conditions, and separated to obtain high L-ribose content fractions while removing L-ribulose content fractions. The high L-ribose content fractions were pooled, concentrated, admixed with a seed crystal to crystallize L-ribose under stirring conditions, followed by separating the mixture to obtain a solid product containing L-ribose crystal. HPLC analysis as described in Example 5 revealed that the purity of the product was about 98 w/w %, and the yield of the L-ribose crystal to the material L-ribulose was about 20%, d.s.b. The crystal can be arbitrarily used in foods, cosmetics, pharmaceuticals, and their materials as a sweetener, quality-improving agent, humectant and replication inhibitory agent for nucleic acids. The recovered immobilized enzyme can be repeatedly used in the present conversion reaction. Furthermore, the high L-ribulose content fractions, which were fractionated and removed from reaction mixtures, can be advantageously recycled as a material for L-ribose to increase the yield of L-ribose crystal.

EXAMPLE 6

Production of L-ribose from Ribitol

One hundred ml aliquots of a nutrient culture medium, consisting of 2 w/v % trypton soya broth, one w/v % glycerol and water, and distributed to two 500-ml shaking flasks, followed by autoclaving the flasks at 120° C. for 20 min. Thereafter, the flasks were cooled and inoculated with a seed of *Acetobacter aceti* (IFO 3281) using a platinum loop, followed by the incubation at 30° C. for 2 days under shaking conditions to obtain a seed culture. 16.8 L of a nutrient culture medium, consisting of 1.1 w/v % polypeptone, 0.2 w/v % "HINUTE SMP", a peptide solution of edible soy beans commercialized by Fuji Oil Co., Ltd., Tokyo, Japan, 1.68 w/v % potassium dihydrogenphosphate, one w/v % glycerine and water, was placed in a 30-L jar fermenter, autoclaved at 120° C. for 20 min, cooled to 30° C., and adjusted to pH 7.2 by the addition of aqueous sodium hydroxide solution. To the nutrient culture medium was inoculated one v/v % of the above seed culture and incubated at 30° C. for 22 hours under aeration-agitation conditions, then mixed with 3.2 L aqueous ribitol solution containing 2 kg ribitol, which had been autoclaved at 120° C. for 20 min, and stirred for 27 hours under aeration-agitation conditions to convert ribitol into L-ribulose. The reaction mixture was membrane filtered to obtain a filtrate. HPLC analysis as described in Example 5 revealed that the filtrate contained at least 97 w/w % L-ribulose, d.s.b.

Using the obtained L-ribulose, L-ribose was prepared as follows: A seed of *Acinetobacter calcoaceticus* LR7C (FERM BP-5335) was inoculated into and incubated in a nutrient culture medium, containing D-lyxose as a carbon source, at 30° C. for 4 days under shaking conditions. A portion of the culture was inoculated into and incubated in a fresh preparation of the same nutrient culture medium for 2 days, and this culturing step was repeated 5 times. After completion of these successive cultures, a portion of the final culture was incubated unto the surface of a nutrient agar plate containing D-lyxose as a carbon source and cultured to form homogenous colonies. One of the colonies as a seed was inoculated into a nutrient culture medium, consisting of 0.5 w/v % yeast extract, 0.5 w/v % polypeptone, 0.5 w/v % salt and water, which had been autoclaved at 120° C. for 20 min, and cultured at 30° C. under shaking conditions to obtain a seed culture. Fifteen L of a fresh preparation of the same nutrient culture medium used in the above seed culture was placed in a 30-L jar fermenter, autoclaved at 120° C. for 20 min, cooled to 30° C., inoculated with one v/v % of the seed culture, and cultured at 30° C. for 20 hours under aeration-agitation conditions. Thereafter, the culture was centrifuged to obtain wet cells, and about 50 g of which was treated with toluene, mixed with 50 mM glycine buffer (pH 9.0) in a volume of one ml per g wet cells to obtain a 110 ml enzyme solution containing 128 units/ml of L-ribose isomerase. The above filtrate containing L-ribulose obtained by the above method was adjusted to pH 9.0 by the addition of aqueous sodium hydroxide solution, mixed with manganese chloride to give a final concentration of 0.5 mM, mixed with about 5 units/g L-ribulose of the enzyme solution, and incubated at 30° C. for 24 hours to convert about 70% L-ribulose into L-ribose.

The reaction mixture thus obtained was filtered with an ultrafilter, desalted and concentrated in vacuo to obtain 1.77 kg of an about 85 w/w t syrup. Ethanol was added to the syrup to crystallize L-ribose, and the crystal was separated, washed, dried in vacuo and pulverized to obtain an about 600 g high-purity L-ribose crystal. HPLC analysis as described in Example 5 confirmed that the purity of the L-ribose crystal was about 99.9 w/w %, d.s.b. The yield of the L-ribose crystal to the material ribitol was about 30%. "GEIGERFLEX RAD-IIB", an x-ray diffraction analyzer using CuKa ray commercialized by Rigaku Corporation, Tokyo, Japan, revealed that the L-ribose crystal had diffraction angles (2 θ) of 16.3°, 20.1°, 21.3°, 21.4° and 33.0°. The L-ribose crystal can be arbitrarily used in food products, cosmetics, pharmaceuticals, and their materials as a sweetener, quality-improving agent, humectant or replication inhibitory agent for nucleic acids.

As is evident from the above, the present L-ribose isomerase acts on L-ribose, D-lyxose, D-talose, D-mannose, L-allose and L-gulose to convert or isomerize them into their corresponding L-ribulose, D-xylulose, D-tagatose, D-fructose, L-psicose and L-sorbose, respectively. The enzymatic reaction is a reversible equilibrium reaction. Thus, the L-ribose isomerase can be used in the isomerization conversion reactions between the aldoses and ketoses. The L-ribose isomerase should not necessarily be allowed to act on its substrates after purified to a relatively-high level, and crude preparations of the L-ribose isomerase can be arbitrarily used to industrially produce rare saccharides. The present invention enables a readily production of rare saccharides which have not been readily available and will greatly influence on the fields of food, cosmetic, pharmaceutical and chemical industries. Therefore, the present invention has unfathomable industrial significance.

While there has been described what is at present considered to be the preferred embodiments of the invention, it will be understood the various modifications may be made therein, and it is intended to cover in the appended claims all such modifications as fall within the true spirit and scope of the invention.

What is claimed is:

1. A process for producing an L-ribose isomerase which isomerizes L-ribose into L-ribulose and vice versa, comprising culturing in a nutrient culture medium a microorganism capable of producing the L-ribose isomerase to form the L-ribose isomerase, and collecting the produced L-ribose isomerase from the culture.

2. The process of claim 1, wherein said microorganism is one of the genus Acinetobacter.

3. The process of claim 2, wherein said microorganism is one selected from the group consisting of *Acinetobacter calcoaceticus* LR7C (FERM BP-5335) and mutants thereof.

4. An isolated microorganism of the genus Acinetobacter which produces an L-ribose isomerase capable of converting L-ribose into L-ribulose and vice versa.

5. The microorganism of claim 4, which is one selected from the group consisting of *Acinetobacter calcoaceticus* LR7C (FERM BP-5335) and mutants thereof.

6. A solid composition which contains an L-ribose crystal and L-ribulose obtainable by a process comprising contacting an L-ribose isomerase capable of converting L-ribose into L-ribulose and vice versa, with L-ribulose to produce L-ribose; crystallizing the resulting mixture containing L-ribose and L-ribulose; and collecting an L-ribose crystal containing L-ribulose.

7. The solid composition of claim 6, wherein said L-ribose crystal has main diffraction angles (2θ) of 16.3°, 20.1°, 21.3°, 21.4° and 33°.

* * * * *

UNITED STATES PATENT AND TRADEMARK OFFICE
CERTIFICATE OF CORRECTION

PATENT NO. : 6,294,369 B1
DATED : September 25, 2001
INVENTOR(S) : Ken Izumori and Keiji Tsusaki It is certified that error appears in the above-identified patent and that said Letters Patent is hereby corrected as shown below:

<u>Title page,</u>
Item [22], Filed, delete "May 31, 2000" and insert therefor -- March 13, 2000 --.

Signed and Sealed this

Twenty-sixth Day of October, 2004

JON W. DUDAS
*Director of the United States Patent and Trademark Office*